United States Patent
Buck, Jr. et al.

(10) Patent No.: US 10,429,336 B2
(45) Date of Patent: Oct. 1, 2019

(54) ELECTRODE ARRANGEMENTS FOR TEST ELEMENT INTEGRITY

(71) Applicant: Roche Diabetes Care, Inc., Indianapolis, IN (US)

(72) Inventors: Harvey Buck, Jr., Indianapolis, IN (US); Walter Jernigan, Carmel, IN (US)

(73) Assignee: Roche Diabeters Care, Inc., Indianapolis, IN (US)

( * ) Notice: Subject to any disclaimer, the term of this patent is extended or adjusted under 35 U.S.C. 154(b) by 0 days.

(21) Appl. No.: 15/314,783

(22) PCT Filed: Jun. 1, 2015

(86) PCT No.: PCT/US2015/033577
§ 371 (c)(1),
(2) Date: Nov. 29, 2016

(87) PCT Pub. No.: WO2015/187580
PCT Pub. Date: Dec. 10, 2015

(65) Prior Publication Data
US 2017/0122896 A1    May 4, 2017

Related U.S. Application Data

(60) Provisional application No. 62/008,160, filed on Jun. 5, 2014.

(51) Int. Cl.
*G01N 27/327*    (2006.01)

(52) U.S. Cl.
CPC ..... *G01N 27/3274* (2013.01); *G01N 27/3272* (2013.01)

(58) Field of Classification Search
CPC .......................................... G01N 27/327–3278
See application file for complete search history.

(56) References Cited

U.S. PATENT DOCUMENTS

| | | |
|---|---|---|
| 5,282,950 A | 2/1994 | Dietze et al. |
| 8,992,750 B1 * | 3/2015 | Beaty ............. G01N 27/3272 204/194 |

(Continued)

FOREIGN PATENT DOCUMENTS

| | | |
|---|---|---|
| EP | 1143245 A2 | 10/2001 |
| JP | 2013518264 A | 5/2013 |

(Continued)

*Primary Examiner* — J. Christopher Ball
(74) *Attorney, Agent, or Firm* — Stinson LLP (57) ABSTRACT

A method is provided for verifying test element integrity includes providing a biosensor having an electrode-support substrate. A first electrode is provided on the substrate that includes a first body and a neck extending from the first body. A second electrode is provided on the substrate that includes a second body and an opposite pair of necks. Each of the necks extends from a respective end of the second body. A spacer is positioned on the substrate and has an edge defining a boundary of a capillary channel formed between a cover and the substrate. The method also includes applying a signal across the necks of the second electrode to verify continuity along the second electrode. The second body of the second electrode and the pair of connective necks surround the first electrode in the capillary channel forming a loop circuit around the first electrode.

16 Claims, 6 Drawing Sheets

(56) References Cited

U.S. PATENT DOCUMENTS

| | | |
|---|---|---|
| 2005/0279631 A1 | 12/2005 | Celentano |
| 2005/0284758 A1 | 12/2005 | Funke et al. |
| 2005/0284773 A1 | 12/2005 | Allen |
| 2013/0140176 A1 | 6/2013 | Beaty et al. |

FOREIGN PATENT DOCUMENTS

| | | |
|---|---|---|
| WO | 20090076263 A1 | 6/2009 |
| WO | 2011092010 A1 | 8/2011 |
| WO | 2012064645 A2 | 5/2012 |

* cited by examiner

ELECTRODE ARRANGEMENTS FOR TEST ELEMENT INTEGRITY

CROSS-REFERENCE TO RELATED APPLICATIONS

This patent application claims priority to and the benefit of International Publication Number WO2015/187580, filed on Jun. 1, 2015, which claims priority to and the benefit of U.S. Provisional Patent Application No. 62/008,160 (filed 5 Jun. 2014), both of which are incorporated herein by reference as if set forth in their entireties.

TECHNICAL FIELD

This patent application relates generally to engineering and medical diagnostics, and more particularly, it relates to an electrode arrangement for test elements, such as biosensor test strips, having an electrode/electrode arranged for verifying test element integrity.

BACKGROUND

Systems, apparatuses and methods for assaying biological fluids, as well as test elements for use therein, are well known. For example, electrochemical-based testing methods are known that generally rely upon a correlation between a current (amperometry), a potential (potentiometry) or an accumulated charge (coulometry) and an analyte concentration, typically in conjunction with a reagent that produces charged-carriers when combined with an analyte of interest. Known test elements for conducting such electrochemical tests are typically disposable biosensor test strips having a detection reagent that chemically reacts with the analyte of interest in a biological fluid sample. Generally, the test element is attached/inserted into a test meter that can measure the reaction between the analyte and the detection reagent to determine the analyte concentration.

In general, test elements have a reaction zone that contains measurement electrodes that come into direct contact with the biological fluid sample. In some amperometric and coulometric electrochemical measurement systems, the measurement electrodes are attached to electronic circuitry in a test meter that supplies an electrical potential to the measurement electrodes and measures the response of the electrochemical sensor to this potential (e.g., current, impedance, charge, etc.). This response is proportional to the analyte concentration.

For test elements in which the electrodes, traces and contact pads are made from electrically conductive thin films (e.g., noble metals, carbon ink, silver paste, etc.), resistivity of the conductive traces that connect the reaction zone of the test element to the electronic circuitry in a test meter can measure several hundred Ohms or more. This resistance causes a potential drop along the length of the traces, such that the potential presented to the measurement electrodes in the reaction zone is less than the potential applied by the test meter to contact pads of the test strip in a contact zone of the test strip. Physical damage to test elements, such as abrasion, cracks, scratches, chemical degradation, etc. can occur during manufacturing, shipping, storage or user mishandling. Such defects can damage test elements so that they may present an extremely high resistance or even an open circuit to the test meter. Such changes in the trace resistance can prevent the test meter from performing an accurate test. Accordingly, a need exists for improved test elements capable of confirming, checking or verifying test element integrity prior to their individual use.

BRIEF SUMMARY

Briefly, an inventive concept described herein includes providing at least one integrity electrode arrangement on test elements. The inventive concept can be achieved either by providing a distinct integrity electrode through which a signal can be applied to verify test element integrity or by providing, for example, a unique counter electrode design through which a signal can be applied to verify test element integrity. When undamaged, the integrity electrode arrangement permits a user to check that there is continuity along electrode(s), substrate and/or detection reagent. The inventive concept therefore is embodied in exemplary systems, apparatuses, devices, test elements and methods as described herein.

For example, methods are provided for verifying integrity of a test element having an integrity electrode arrangement. The methods include providing a test element having an electrode-support substrate upon which a first electrode is disposed. The first electrode includes a first body portion and a connective neck extending from the first body portion. The electrode-support substrate also has a second electrode disposed thereupon, where the second electrode includes a second body portion and an opposite pair of connective necks. Each one of the opposite pair of connective necks extends from a respective end of the second body portion. In addition, a spacer is disposed on the electrode-support substrate, where the spacer includes at least one edge defining a boundary of a capillary channel formed between a cover and the electrode-support substrate. Moreover, the methods include applying a signal across the pair of connective necks of the second electrode to verify continuity along the second electrode. The second body portion of the second electrode and the opposite pair of connective necks surround the first electrode in the capillary channel forming a loop circuit around the first electrode.

Alternative methods are provided for verifying integrity of a test element having an integrity electrode arrangement. The methods can include providing a test element as described herein that includes a capillary channel defined thereon. Here, a first electrode is provided on the electrode-support substrate, at least a portion of the first electrode being formed in the capillary channel. In addition, at least two sample sufficiency electrodes are provided on the electrode-support substrate, each of the sample sufficiency electrodes being positioned along a respective side edge of the electrode-support substrate, the sample sufficiency electrodes defining a gap therebetween. Moreover, an integrity electrode is provided on the electrode-support substrate in the capillary channel, the integrity electrode being coupled to and extending between the at least two sample sufficiency electrodes. In addition, the methods include applying a signal across the at least two sample sufficiency electrodes to verify continuity across the integrity electrode. The integrity electrode and the at least two sample sufficiency electrodes surround the first electrode in the capillary channel forming a loop circuit around the first electrode.

In view of the methods above, test elements also are provided. The test elements include an electrode-support substrate having a capillary channel defined thereon at a first end of the electrode-support substrate. The test elements also include a first electrode disposed on the electrode-support substrate, which has a first body portion and a connective neck extending from the first body portion. The test elements also include a second electrode disposed on the electrode-support substrate, which has a second body portion and at least two connective necks. Each one of the at least two connective necks extends from a respective end of the second body portion. Furthermore, the test elements include a spacer positioned on the electrode-support substrate, which has at least one edge defining a boundary of the capillary channel. Moreover, the test elements include a cover coupled to the spacer. The second body portion of the second electrode and the at least two connective necks form a U-shaped loop circuit surrounding the first electrode, where the second electrode is configured to provide an indication of continuity to verify test element integrity.

Alternative test elements are provided that include an electrode-support substrate having a capillary channel defined thereon at a first end of the electrode-support substrate. The test elements also include a first electrode disposed on the electrode-support substrate, which has a first body portion and a connective neck extending from the first body portion. The test elements also include a second electrode disposed on the electrode-support substrate, which has a second body portion and at least two connective necks. Each one of the at least two connective necks extends from a respective end of the second body portion. Furthermore, the test elements include a spacer positioned on the electrode-support substrate, which has at least one edge defining a boundary of the capillary channel. In addition, the test elements include a cover coupled to the spacer. Moreover, the test elements include at least two sample sufficiency electrodes disposed on the electrode-support substrate. Each one of the sample sufficiency electrodes is positioned along a respective side edge of the electrode-support substrate. Likewise, the test elements include an integrity electrode disposed on the electrode-support substrate, which is coupled to and extends between the at least two sample sufficiency electrodes. The integrity electrode is configured to provide an indication of continuity to verify test element integrity.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DETAILED DESCRIPTION OF EXEMPLARY EMBODIMENTS

Overview

The systems, apparatuses, devices, test elements and methods now will be described more fully hereinafter with reference to the accompanying drawings, in which some, but not all embodiments of the inventive concept are shown. Indeed, the systems, apparatuses, devices, test elements and methods may be embodied in many different forms and should not be construed as limited to the embodiments set forth herein; rather, these embodiments are provided so that this disclosure will satisfy applicable legal requirements.

Likewise, many modifications and other embodiments of the systems, apparatuses, devices, test elements and methods described herein will come to mind to one of skill in the art to which the disclosure pertains having the benefit of the teachings presented in the foregoing descriptions and the associated drawings. Therefore, it is to be understood that the systems, apparatuses, devices, test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the systems, apparatuses, devices, test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Furthermore, approximating language, as used herein and in the claims, may be applied to modify any quantitative representation that could permissibly vary without resulting in a change in the basic function to which it is related. Accordingly, a value modified by a term or terms, such as "about," "approximately" and "substantially" is not to be limited to the precise value specified. In at least some instances, the approximating language may correspond to the precision of an instrument for measuring the value. Likewise, range limitations may be combined or interchanged; such ranges are identified and include all the sub-ranges contained therein unless context or language indicates otherwise.

For example, as used herein, "about" means within a statistically meaningful range of a value or values such as, for example, a stated concentration, length, width, height, weight, pH, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The systems, apparatuses, devices, test elements and methods are useful in a variety of applications. For example, the test elements can be used to assay a body fluid sample for the presence and/or concentration of an analyte of interest such as, for example, glucose. Because the test elements include an integrity electrode arrangement, a user can have increased confidence that erroneous test results or faulty test elements will be failsafed and either not reported or not used, respectively.

Test Elements

Figure 1:
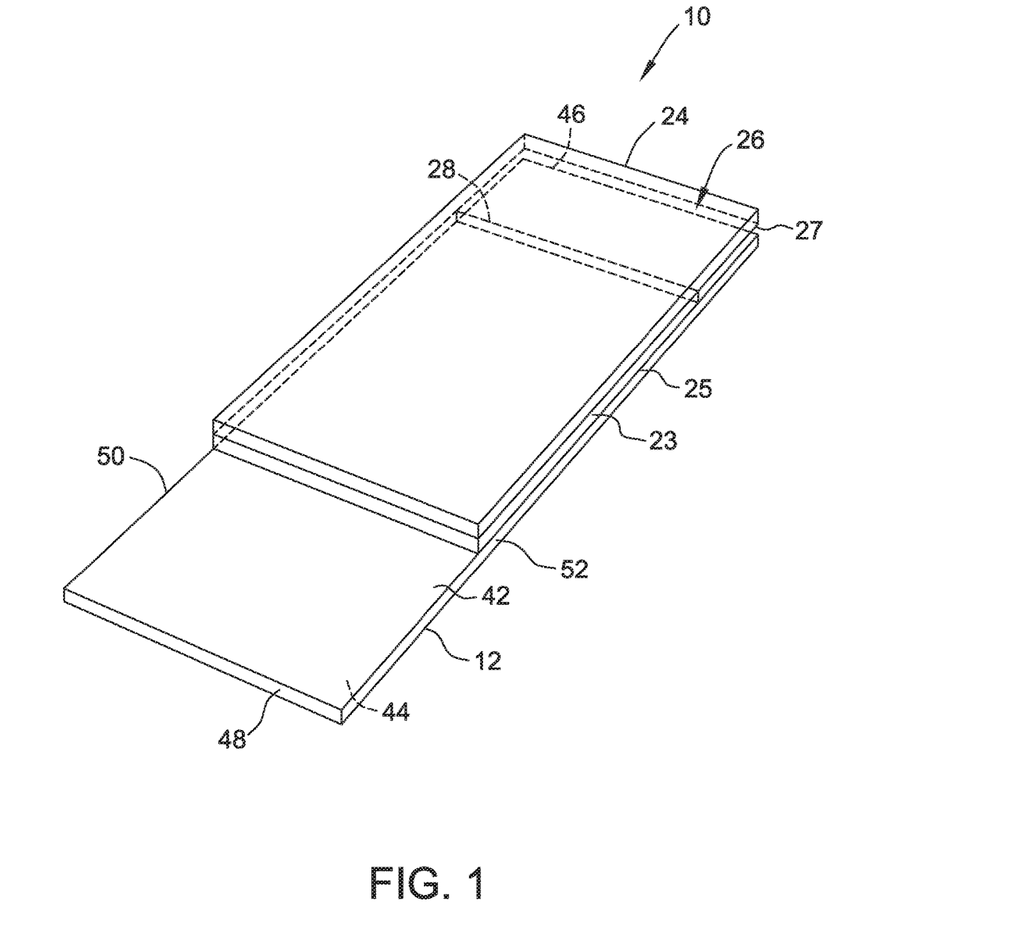
FIG. 1 is a perspective view of an exemplary test element.
Figure 2:
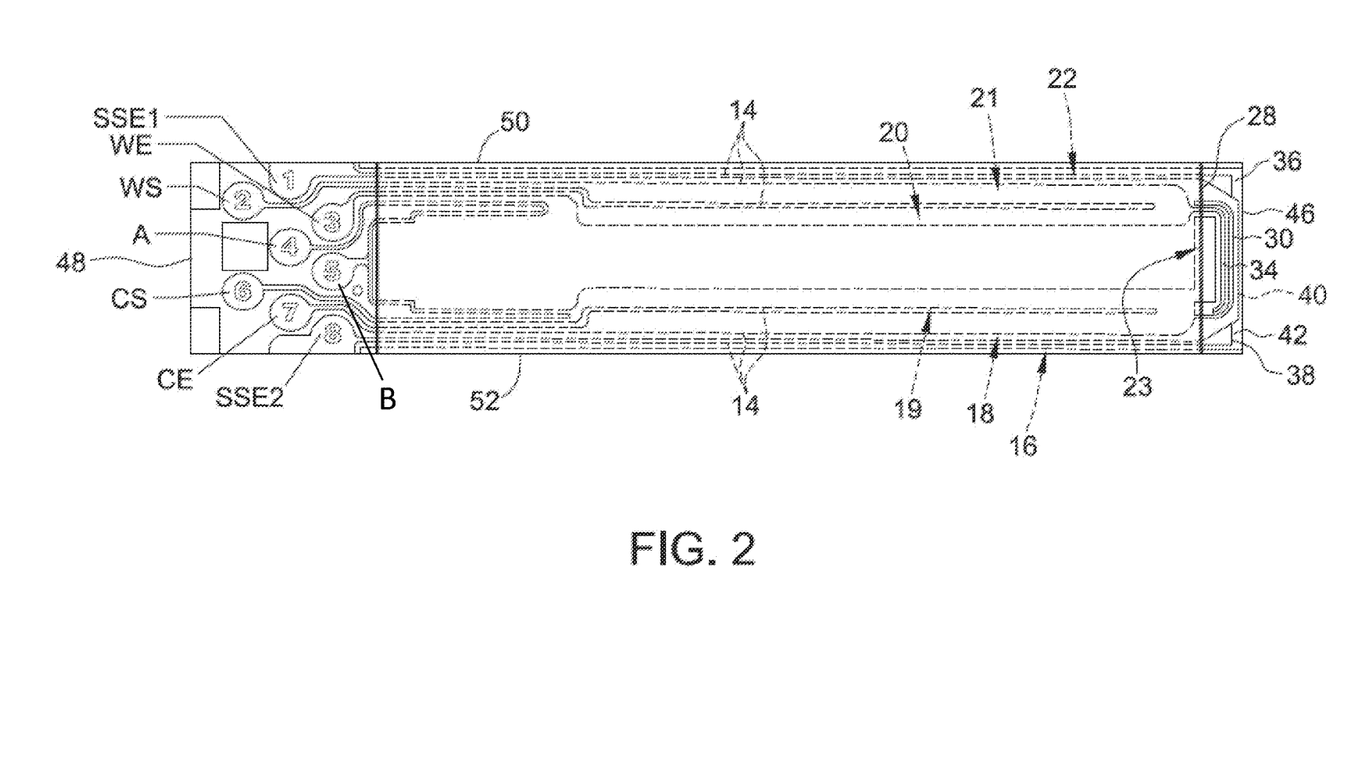
FIG. 2 is a plan view of the test element shown in FIG. 1.
Figure 3:
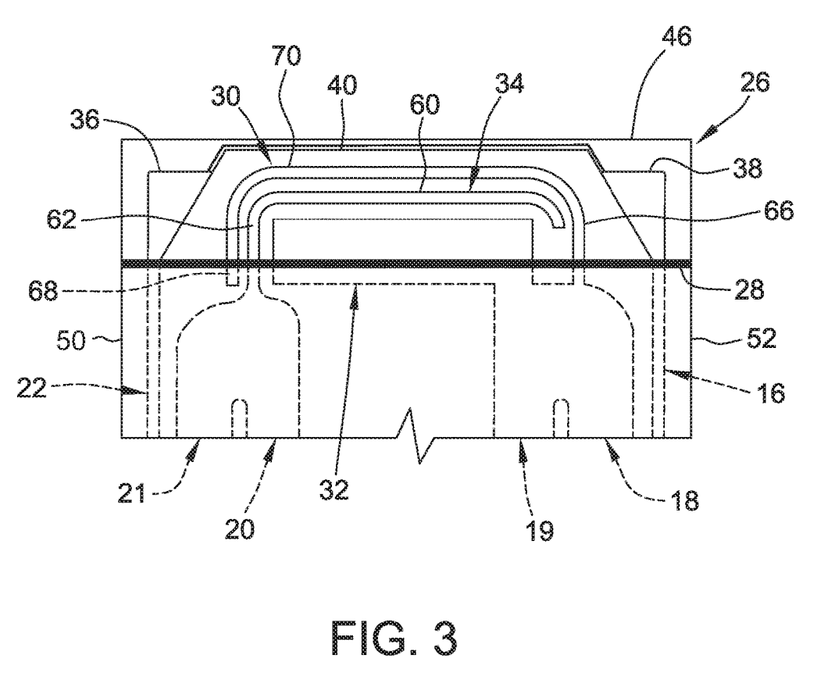
FIG. 3 is a plan view of a portion of the test element shown in FIG. 1 showing an exemplary electrode arrangement including an integrity electrode.

FIG. 1 is a perspective view of an exemplary test element 10. FIG. 2 is a plan view of the test element 10 shown in FIG. 1. FIG. 3 is a plan view of a portion of the test element 10 shown in FIG. 1 showing an exemplary electrode arrangement including an integrity electrode 40. In the exemplary embodiment, the test element 10 includes an electrode-support substrate 12, an electrical conductor 14 formed on the electrode-support substrate 12 that defines a plurality of electrode traces 16, 18, 19, 20, 21 and 22, a spacer 23 positioned on the electrode-support substrate 12, and a cover 24 positioned on the spacer 23. In some instances, the electrical conductor 14 may form any number of electrode traces that enable the test element 10 to function as described herein. In FIGS. 2 and 3, however, the spacer 23 is not shown for clarity.

As shown in FIGS. 1 and 2, the test element 10 can have a substantially rectangular shape; however, any one of a number of forms that enable the test element 10 to function as described herein also are contemplated. In addition, the test element 10 can be any one of a plurality produced from rolls of material, sheets of material or any other material stock in accordance with the principles of this disclosure. In general, the material selection for fabricating the test element 10 includes any material that is sufficiently flexible for roll processing, but is rigid enough to give a useful stiffness to the finished test element 10.

In the exemplary embodiment, the electrode-support substrate 12 of the test element 10 includes a first surface 42 facing the spacer 23 and a second surface 44 opposite the first surface 42. Moreover, the electrode-support substrate 12 has opposite first and second ends 46, 48 and opposite side edges 50, 52 that extend between the first and second ends 46, 48. In some instances, the first and second ends 46, 48 and the opposite side edges 50, 52 of the electrode-support substrate 12 form a generally rectangular shape. Alternatively, the first and second ends 46, 48 and the opposite side edges 50, 52 may be arranged to form any one of a variety of shapes and sizes that enable the test element 10 to function as described herein. In some instances, the electrode-support substrate 12 can be fabricated of a flexible polymer including, but not limited to, a polyester or polyimide, such as polyethylene naphthalate (PEN). Alternatively, the electrode-support substrate 12 can be fabricated from any other suitable materials that enable the electrode-support substrate 12 to function as described herein.

In the exemplary embodiment, the electrical conductor 14 forming the electrode traces 16, 18, 19, 20, 21 and 22 is provided on the first surface 42 of the electrode-support substrate 12. The electrical conductor 14 may be fabricated from materials including, but not limited to, aluminum, carbon (e.g., graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., highly doped polycrystalline silicon), silver, tantalum, tin, titanium, tungsten, uranium, vanadium, zinc, zirconium, and combinations thereof. In some instances, the electrode traces 16, 18, 19, 20, 21 and 22 are isolated from the rest of the electrical conductor 14 by laser ablation or laser scribing, both of which are well known in the art. In this manner, the electrode traces 16, 18, 19, 20, 21 and 22 can be fabricated by removing the electrical conductor 14 from an area extending around the electrodes either broadly, such as by broad field ablation, or minimally, such as by line scribing. Alternatively, the electrode traces 16, 18, 19, 20, 21 and 22 may be fabricated by other techniques such as, for example, lamination, screen-printing, photolithography, etc.

In the exemplary embodiment, test element 10 is a full width end dose ("FWED"; having a capillary channel bounded on one side) test element, which has a capillary channel 26 or an inlet at the first end 46 of the electrode-support substrate. It is contemplated, however, that the capillary channel also can be a conventional capillary channel (i.e., bounded on more than one side). In a FWED test element, the spacer 23 extends between the opposite side edges 50, 52 of the electrode-support substrate 12 to form the capillary channel in part with a cover. It is contemplated that the spacer 23 may be fabricated of a single component or even a plurality of components. Regardless, the spacer 23 should include an end edge 28 substantially parallel to and facing the first end 46 of the electrode-support substrate 12, thereby defining a boundary of a capillary channel 26 by extending across the entire width of the electrode-support substrate 12. Alternatively, and as noted above, the end edge 28 may include multiple portions located between the first and second ends 46, 48 and the opposite side edges 50, 52 of the electrode-support substrate 12 to form a generally U-shaped pattern to define the boundary of the capillary channel 26 having a sample inlet at the first end 46 of the test element 10 (not shown). Other suitable embodiments contemplate an end edge 28 that forms hemi-ovular, semicircular, or other shaped capillary channels, and the one or more of the portions of end edge 28 may include linear or non-linear edges along all or part of its length (not shown).

The spacer 23 is fabricated from an insulative material such as, for example, a flexible polymer including an adhesive coated polyethylene terephthalate (PET)-polyester. One particular non-limiting example of a suitable material includes a white PET film, both sides of which are coated with a pressure-sensitive adhesive. The spacer 23 may be constructed of a variety of materials and includes an inner surface 25 that may be coupled to the first surface 42 of the electrode-support substrate 12 using any one or a combination of a wide variety of commercially available adhesives. Additionally, when first surface 42 of the support substrate 12 is exposed and not covered by the electrical conductor 14, the cover 24 may be coupled to support the electrode-substrate 12 by welding, such as heat or ultrasonic welding. It also is contemplated that first surface 42 of the electrode-support substrate 12 may be printed with, for example, product labeling or instructions (not shown) for use of the test elements 10.

Further, in the exemplary embodiment, the cover 24 extends between the opposite side edges 50, 52 of the electrode-support substrate 12 and extends to the first end 46 of the electrode-support substrate 12. Alternatively, the cover 24 may extend beyond the first end 46 a predefined distance that enables the test element 10 to function as described herein. In the exemplary embodiment, the capillary channel 26 is therefore defined as the space between the cover 24 and the electrode-support substrate 12, bounded by the first end 46 and the opposite side edges 50, 52 of the electrode-support substrate 12 and the end edge 28 of the spacer 23.

The cover 24 can be fabricated from an insulative material such as, for example, a flexible polymer including an adhesive coated polyethylene terephthalate (PET)-polyester. One particular non-limiting example of a suitable material includes a transparent or translucent PET film. The cover 24 may be constructed of a variety of materials and includes a lower surface 27 that may be coupled to the spacer 23 using any one or a combination of a wide variety of commercially available adhesives. Additionally, the cover 24 may be coupled to the spacer 23 by welding, such as heat or ultrasonic welding.

In the exemplary embodiment, the test element 10 includes an outer counter electrode 30 and an inner counter electrode 32 extending across the capillary channel 26 and coupled to electrode traces 18 and 19. In addition, the test element 10 includes a working electrode 34 that is positioned in capillary channel 26 between the counter electrodes 30, 32. The working electrode 34 is coupled to traces 20 and 21. Moreover, the test element 10 also includes a sample sufficiency working electrode (SSWE) 36 coupled to electrode trace 22 and a sample sufficiency counter electrode (SSCE) 38 coupled to electrode trace 16 positioned in the capillary channel 26. The SSWE 36 and the SSCE 38 are positioned adjacent the edges of the electrode-support substrate 12. Extending between the SSWE 36 and the SSCE 38 is the integrity electrode 40.

In the exemplary embodiment, the SSCE 36 is coupled to contact pad SSE1 by electrode trace 22, and the SSCE 38 is coupled to contact pad SSE2 by electrode trace 16. Likewise, the outer counter electrode 30 and the inner counter electrode 32 are coupled to electrode traces 18, 19. As shown in FIG. 2, the electrode trace 18 is coupled to contact pad CE, and the electrode trace 19 is coupled to contact pads CS, B and A. Moreover, the working electrode 34 is coupled to electrode traces 20 and 21, where electrode trace 20 is coupled to the contact pad WE, and the electrode trace 21 is coupled to the contact pad WS. These contact pads provide a conductive area upon the test element 10 to be contacted by a connector contact of a test meter (not shown) once the test element 10 is inserted into the test meter. It is further contemplated that the configuration of the electrodes, the number of electrodes, as well as the spacing between the electrodes may vary in accordance with the disclosure. Consequently, test element 10 may include more or fewer than the number of electrodes illustrated herein.

In the exemplary embodiment, the working electrode 34 defines an effective working electrode area in the capillary channel 26. The effective working electrode area is the area of the working electrode that contacts a fluid sample in the capillary channel 26 when the capillary channel 26 includes sufficient volume of the fluid sample to initiate a measurement sequence. As seen in FIG. 3, the working electrode 34 includes a main body portion 60 extending laterally between the opposite side edges 50, 52 of the electrode-support substrate 12, and a connective neck 62 extending from main body portion 60 across the edge 28 of capillary channel 26 (i.e., transversely from the main body portion 60 toward the end 48 of test 10 opposite capillary channel 26). The connective neck 62 is coupled to the electrode traces 20, 21 that extend along one side of the electrode-support substrate 12. The spacer 23 is positioned such that the edge 28 extends across the connective neck 62 and so that the main body portion 60 is located entirely within the capillary channel 26. Electrochemical detection reagents can be positioned on the working electrode 34, which provide electrochemical probes for specific analytes. The choice of specific reagents depends on the analyte(s) to be measured, which are well known in the art. An example of a detection reagent that may be used in the test element 10 is a reagent for measuring glucose from a body fluid sample such as a whole blood sample.

In the exemplary embodiment, the inner counter electrode 32 and the outer counter electrode 30 are connected to electrode traces 18, 19 that extend along one side of the electrode-support substrate 12. The outer electrode 30 extends laterally between the opposite side edges 50, 52 of the electrode-support substrate 12, and includes an extension trace 68 and a connective neck 66 that each extend from a main body portion 70 across the edge 28 of capillary channel 26 (i.e., transversely from the main body portion 70 toward the end 48 of test element 10 opposite capillary channel 26). Moreover, the edge 28 of the capillary channel 26 extends along and partially overlaps the inner counter electrode 32. In some instances, electrochemical detection reagents can be positioned on the inner counter electrode 32 and the outer counter electrode 30. As noted above, the detection reagents provide electrochemical probes for specific analytes and are well known in the art, especially for measuring glucose.

In one form of the inventive concept, the integrity electrode 40 extends between the SSWE 36 and the SSCE 38 proximate the end 46 of the electrode-support substrate 12. As seen in FIG. 3, the working electrode 34 and both the inner and the outer counter electrodes 30, 32 are positioned in a region of the electrode-support substrate 12 surrounded by the integrity electrode 40, the SSWE 36 and the SSCE 38. The integrity electrode 40 can be formed as a high-resistive trace such as, for example, from a high-resistive material (e.g., carbon) or a thin trace of a low-resistive material (e.g., gold). In some instances, the integrity electrode 40 has a resistance that ranges between about $1/10$ of the sample resistance between the SSWE 36 and the SSCE 38 to about 1 megaohm (Mohm). If the resistance of the integrity electrode 40 is too small, the test meter may not be able to detect a sample sufficiency with the same electrodes (i.e. the SSWE 36 and the SSCE 38). However, if the resistance of the integrity electrode 40 is too large, then a test element being used in a humid condition and having a broken integrity electrode 40 may appear to the test meter to have the same conductivity as an intact integrity electrode.

In operation, the integrity electrode 40 is configured to provide an indication of the test element integrity. For example, the end 46 of the test element 10 may sustain physical damage, such as abrasion, cracks, scratches, chemical degradation, etc. that results in a discontinuity along the integrity electrode 40 and one or more of the electrodes 30, 32 and 34. The test meter or other device configured to use test element 10 is configured to apply a signal such as, for example, an AC signal, to the test element 10 to check the electrical continuity between the SSWE 36 and the SSCE 38 along the integrity electrode 40 prior to using the test element 10 to analyze biological fluids. A discontinuity along the integrity electrode 40 results in an indication that the test element 10 has likely sustained physical damage. Thus, the test meter can alert the user that the test element 10 has failed the integrity check, and therefore, should be discarded. In some instances, the meter provides a failsafe and does not apply the test sequence used to determine presence and/or concentration of the analyte of interest. If the test element 10 passes the integrity check (i.e., the test meter confirms continuity along the integrity electrode 40), then the meter can alert the user that the test element 10 is safe to use.

In some instances, after confirming continuity along the integrity electrode 40, the test meter can apply an overvoltage to the integrity electrode 40. As used herein, "overvoltage" means a voltage above the upper design limit of the circuit receiving the overvoltage. During the overvoltage condition the integrity electrode 40 acts as a fuse, burning out and opening the integrity electrode 40 between the SSWE 36 and the SSCE 38, thus enabling the test meter to detect sufficiency of the sample volume, based on the electrical response between the SSWE 36 and the SSCE 38 when the sample has reached a sufficient extent in the capillary channel 26. Alternatively, the integrity electrode 40 can be left undisturbed and the meter can be configured to obtain a sample sufficiency indication between the SSWE 36 and the SSCE 38 with the integrity electrode 40 in place.

Figure 4:
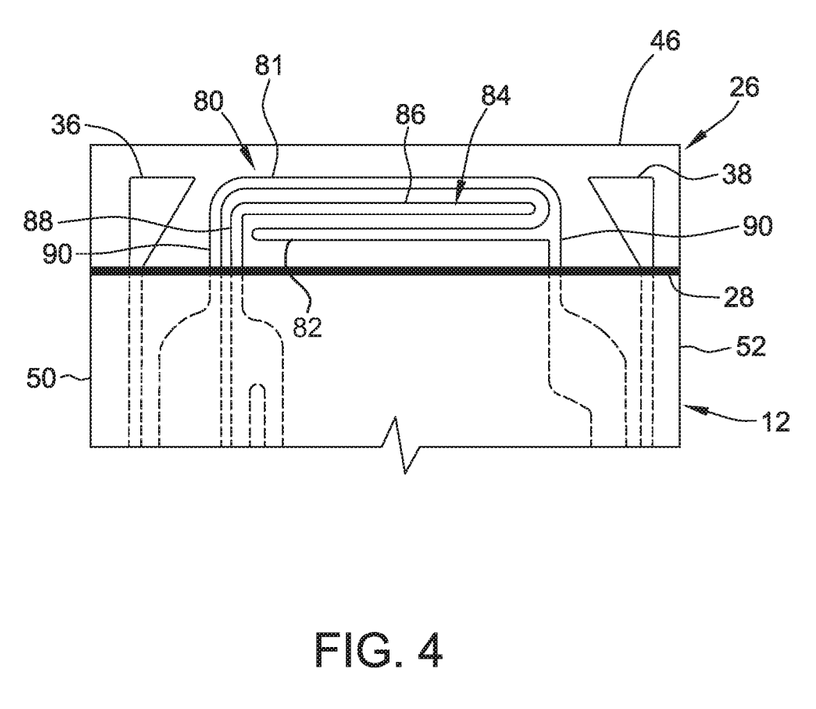
FIG. 4 is a plan view of another embodiment of electrode arrangement for use with the test element shown in FIG. 1.

FIG. 4 is a plan view of another embodiment of electrode arrangement for use with the test element 10 shown in FIG. 1. Here, the test element 10 includes the capillary channel 26 that extends across the entire width of the electrode-support substrate 12 (i.e., FWED). The edge 28 of the capillary channel 26 is formed by the spacer 23. A counter electrode 80 extends across the capillary channel 26, and a working electrode 84 is positioned in the capillary channel 26, surrounded by the counter electrode 80, such that a loop circuit is formed around the working electrode 84. The SSWE 36 and the SSCE 38 are positioned in capillary channel 26 adjacent the edges 50, 52 of the electrode-support substrate 12. The portions of the test element 10 not described can include any of the features of the test elements described herein above.

The working electrode 84 includes a main body portion 86 extending laterally between the side edges 50, 52 of the electrode-support substrate 12, and a connective neck 88 extending from the main body portion 86 across the edge 28 of capillary channel 26 (i.e., transversely from the main body portion 86 toward the end 48 of the test element 10 opposite the capillary channel 26). The spacer 23 is positioned so that the edge 28 extends across the connective neck 88 and so that the main body portion 86 is located entirely within the capillary channel 26.

The counter electrode 80 includes an outer body portion 81 extending laterally between the opposite side edges 50, 52 of the electrode-support substrate 12 adjacent the end 46 of the electrode-support substrate 12, and includes opposite connective necks 90 extending from the outer body portion 81 across the edge 28 of capillary channel 26 (i.e., transversely from the outer body portion 81 toward the end 48 of test element 10 opposite capillary channel 26) forming a generally U-shaped electrode. Moreover, the counter electrode 80 includes an inner body portion 82 extending laterally between the opposite side edges 50, 52 of the electrode-support substrate 12 and connecting to one of the opposite connective necks 90. The outer body portion 81 and the inner body portion 82 of the counter electrode 80 are located entirely within the capillary channel 26.

In another form of the inventive concept, the counter electrode 80 is configured to provide an indication of test element integrity. For example, the end 46 of the test element 10 may sustain physical damage, such as abrasion, cracks, scratches, chemical degradation, etc. that results in a discontinuity along the outer body portion 81 of the counter electrode 80. The test meter or other device configured to use test element 10 is configured to apply a signal such as, for example, an AC signal, to the test element 10 to check the electrical continuity along the counter electrode 80 prior to using the test element 10 to analyze biological fluids. A discontinuity along the counter electrode 80 results in an indication that the test element 10 has likely sustained physical damage. Thus, the test meter can alert the user that the test element 10 has failed the integrity check, and therefore, should be discarded (i.e., test result failsafed). If the test element 10 passes the integrity check (i.e., the test meter confirms continuity along the counter electrode 80), then the meter can alert the user that the test element 10 is safe to use.

Figure 5:
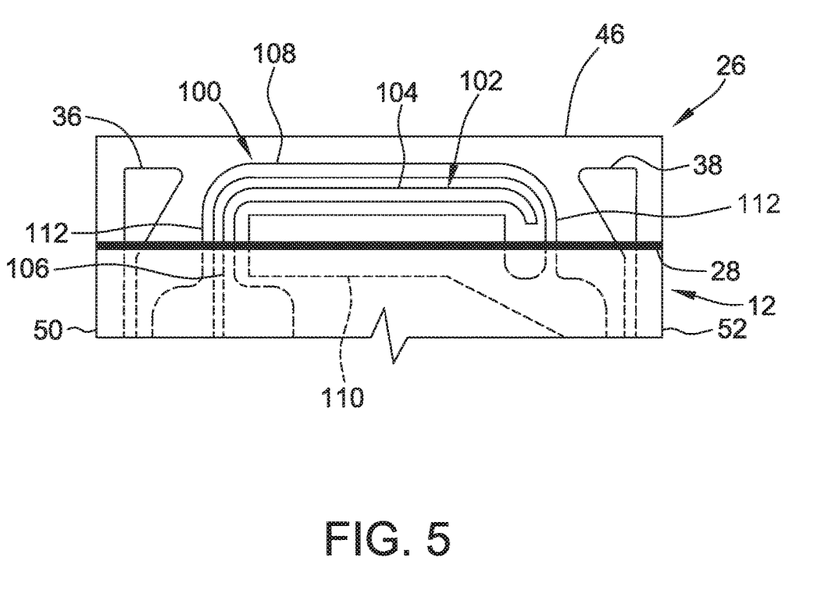
FIG. 5 is a plan view of another embodiment of electrode arrangement for use with the test element shown in FIG. 1.

FIG. 5 is a plan view of another embodiment of electrode arrangement for use with the test element 10 shown in FIG. 1. Again, the test element 10 includes a capillary channel 26 that extends across the entire width of the electrode-support substrate 12 (i.e., FWED). The edge 28 of the capillary channel 26 is formed by the spacer 23. A counter electrode 100 extends across the capillary channel 26, and a working electrode 102 is positioned in the capillary channel 26, surrounded by the counter electrode 100, such that a loop circuit is formed around the working electrode 102. The SSWE 36 and the SSCE 38 are positioned in capillary channel 26 adjacent the edges 50, 52 of the electrode-support substrate 12. The portions of the test element 10 not described can include any of features of the test elements described herein above.

The working electrode 102 includes a main body portion 104 extending laterally between the side edges 50, 52 of the electrode-support substrate 12, and a connective neck 106 extending from the main body portion 104 across the edge 28 of capillary channel 26 (i.e., transversely from the main body portion 104 toward the end 48 of the test element 10 opposite the capillary channel 26). The spacer 23 is positioned so that the edge 28 extends across the connective neck 106 and so that the main body portion 104 is located entirely within the capillary channel 26.

The counter electrode 100 includes an outer body portion 108 extending laterally between the opposite side edges 50, 52 of the electrode-support substrate 12 adjacent the end 46 of the electrode-support substrate 12, and includes opposite connective necks 112 extending from the outer body portion 108 across the edge 28 of capillary channel 26 (i.e., transversely from the outer body portion 108 toward the end 48 of test element 10 opposite capillary channel 26) forming a generally U-shaped electrode. Moreover, the counter electrode 100 includes an inner body portion 110 extending laterally between the opposite side edges 50, 52 of the electrode-support substrate 12 and connecting to one of the opposite connective necks 112. In this embodiment, the edge 28 of the capillary channel 26 extends along and partially overlaps the inner body portion 110. The outer body portion 108, conversely, is located entirely within the capillary channel 26.

As above, the inventive concept includes configuring the counter electrode 100 to provide an indication of test element integrity. For example, the end 46 of the test element 10 may sustain physical damage, such as abrasion, cracks, scratches, chemical degradation, etc. that results in a discontinuity along the outer body portion 108 of the counter electrode 100. The test meter or other device configured to use test element 10 is configured to apply a signal such as, for example, an AC signal, to the test element 10 to check the electrical continuity along the counter electrode 100 prior to using the test element 10 to analyze biological fluids. A discontinuity along the counter electrode 100 results in an indication that the test element 10 has likely sustained physical damage. Thus, the test meter can alert the user that the test element 10 has failed the integrity check, and therefore, should be discarded (i.e., test result failsafed). If the test element 10 passes the integrity check (i.e., the test meter confirms continuity along the counter electrode 100), then the meter can alert the user that the test element 10 is safe to use.

Figure 6:
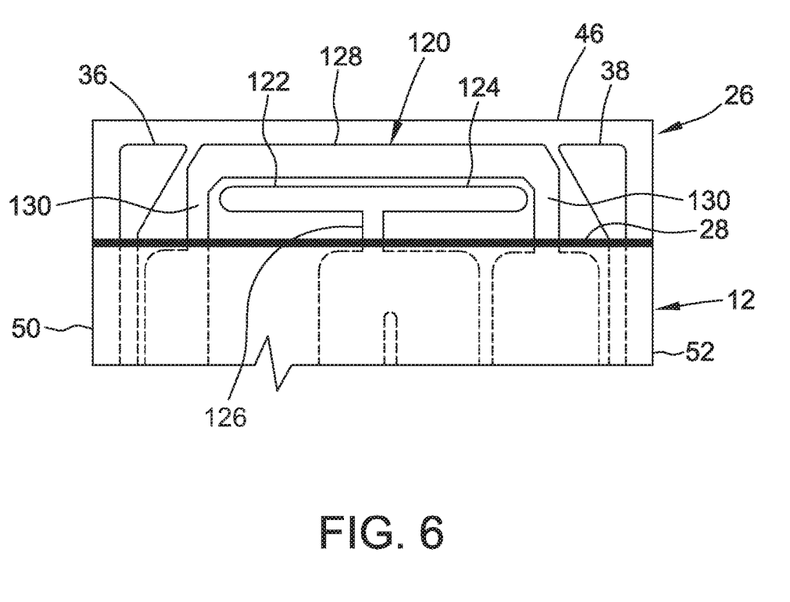
FIG. 6 is a plan view of another embodiment of electrode arrangement for use with the test element shown in FIG. 1.

FIG. 6 is a plan view of another embodiment of electrode arrangement for use with the test element 10 shown in FIG. 1. Again, the test element 10 includes the capillary channel 26 that extends across the entire width of the electrode-support substrate 12 (i.e., FWED). The edge 28 of the capillary channel 26 is formed by the spacer 23. A counter electrode 120 extends across the capillary channel 26, and a working electrode 122 is positioned in the capillary channel 26, surrounded by the counter electrode 120 so that a loop circuit is formed around the working electrode 122. The SSWE 36 and the SSCE 38 are positioned in capillary channel 26 adjacent the edges 50, 52 of the electrode-support substrate 12. The portions of the test element 10 not described can include any of the features of the test elements described herein above.

The working electrode 122 includes a main body portion 124 extending laterally between the side edges 50, 52 of the electrode-support substrate 12, and a connective neck 126 extending from the main body portion 124 across the edge 28 of capillary channel 26 (i.e., transversely from the main body portion 124 toward the end 48 of the test element 10 opposite the capillary channel 26). The cover 24 is positioned so that the edge 28 extends across the connective neck 126 and so that the main body portion 124 is located entirely within the capillary channel 26.

The counter electrode 100 includes a main body portion 128 extending laterally between the opposite side edges 50, 52 of the electrode-support substrate 12 adjacent the end 46 of the electrode-support substrate 12, and includes opposite connective necks 130 extending from the main body portion 128 across the edge 28 of capillary channel 26 (i.e., transversely from the main body portion 128 toward the end 48 of test element 10 opposite capillary channel 26) forming a generally U-shaped electrode. The spacer 23 is positioned such that the edge 28 extends across the opposite connective necks 130 and so that the main body portion 128 is located entirely within the capillary channel 26.

The counter electrode 120 is configured to provide an indication of the integrity of the test element 10. For example, the end 46 of the test element 10 may sustain physical damage, such as abrasion, cracks, scratches, chemical degradation, etc. that results in a discontinuity along the main body portion 128 of the counter electrode 120. The test meter or other device configured to use test element 10 is configured to apply a signal, for example, without limitation, an AC signal, to the test element 10 to check the electrical continuity along the counter electrode 120 prior to use of the test element 10 for testing compositions of biological fluids. A discontinuity along the counter electrode 120 results in an indication that the test element 10 has likely sustained physical damage. Thus, the test meter can alert the user that the test element 10 has failed the integrity check, and therefore, should be discarded. If the test element 10 passes the integrity check (i.e., the test meter confirms continuity along the counter electrode 120), then the meter can alert the user that the test element 10 is safe to use.

Methods

One suitable method of verifying test element integrity of a test element having an integrity electrode arrangement includes providing an electrode-support substrate having at least one working electrode on the support substrate, where the working electrode includes a main body portion and a connective neck extending from an end of the main body portion. Further, a counter electrode is provided on the support substrate. The counter electrode includes a main body portion and an opposite pair of connective necks, wherein each connective neck extends from an opposite end of the main body portion. The counter electrode and the opposite pair of connective necks surround or frame the working electrode in the capillary channel of the test element, forming a loop circuit around the working electrode. Furthermore, a spacer is positioned on the support substrate. The spacer includes an edge that defines a rear boundary of the capillary channel between a cover and the electrode-support substrate. The edge extends across the connective neck of the working electrode so that the main body portion is located entirely within the capillary channel. In addition, the edge extends across the opposite pair of connective necks of the counter electrode so that the main body portion is located entirely within the capillary channel.

Another suitable method of verifying test element integrity of a test element having an integrity electrode arrangement includes providing an electrode-support substrate. The method also includes providing a working electrode on the electrode-support substrate. The working electrode includes a main body portion and a connective neck extending from an end of the main body portion. Further, at least two sample sufficiency electrodes are provided on the support substrate, wherein each of the sample sufficiency electrodes is positioned along a respective side edge of the electrode-support substrate outside the working electrode. In addition, an integrity electrode is provided on the electrode-support substrate and is coupled to each one of the pair of sample sufficiency electrodes. The pair of sample sufficiency electrodes and the integrity electrode surrounds or frames the working electrode in the capillary channel of the test element forming a loop circuit around the working electrode. Moreover, a spacer is positioned on the support substrate, the spacer including an edge that defines a rear boundary of the capillary channel between a cover and the electrode-support substrate. The edge extends across the connective neck of the working electrode so that the main body portion is located entirely within the capillary channel.

In the methods, a signal, such as an AC signal, is applied to the integrity electrode arrangement to test or verify continuity along the integrity electrode arrangement. In some instances, the integrity signal is applied prior to an analyte measurement signal or analyte test sequence. However, it is contemplated that the integrity signal can be applied after the measurement signal or test sequence. Advantageously, the integrity test signal can be the same as known AC signals used to measure sample sufficiency. If the integrity signal indicates a discontinuity, the meter can alert the user that the test element cannot be used and/or that the measurement should be discarded.

The methods also can include applying an overvoltage across the at least two sample sufficiency electrodes when included to burn out and open the integrity electrode. The duration and signal strength for the overvoltage can be readily determined by one of skill in the art.

Exemplary embodiments of electrode arrangements for a test element are described above in detail. The apparatus and methods are not limited to the specific embodiments described herein, but rather, operations of the methods and components of the systems may be utilized independently and separately from other operations or components described herein. For example, the methods and apparatus described herein may have other industrial or consumer applications and are not limited to practice with biosensor components as described herein. Rather, one or more embodiments may be implemented and utilized in connection with other industries.

As various changes could be made in the above constructions without departing from the scope of the present disclosure, it is intended that all matter contained in the above description and shown in the accompanying drawings shall be interpreted as illustrative and not in a limiting sense.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

1. A method of verifying integrity test element of a test element having an integrity electrode arrangement, the method comprising:
providing a test element comprising (a) an electrode-support substrate, (b) a first electrode provided on the electrode-support substrate that includes a first body portion and a connective neck extending from the first body portion, (c) a second electrode provided on the electrode-support substrate that includes a second body portion and an opposite pair of connective necks, each one of the opposite pair of connective necks extending from a respective end of the second body portion, (d) a cover, and (e) a spacer coupled to the electrode-support substrate, the spacer including an edge defining a boundary of a capillary channel formed between the cover and the electrode-support substrate, wherein the second body portion of the second electrode and the opposite pair of connective necks surround the first electrode in the capillary channel forming a loop circuit around the first electrode; and
applying a signal across the pair of connective necks of the second electrode to verify continuity along the second electrode.

2. The method of Embodiment 1, wherein the spacer is positioned so that the edge extends across the connective neck of the first electrode such that the first body portion is located entirely within the capillary channel.

3. The method of Embodiment 1, wherein the spacer is positioned so that the edge extends across the opposite pair of connective necks of the second electrode such that the second body portion is located entirely within the capillary channel.

4. The method of Embodiments 1 to 3, wherein the second electrode further comprises a third body portion positioned adjacent the first body portion of the first electrode opposite the second body portion of the second electrode, and wherein the third body portion is coupled to one of the opposite pair of connective necks.

5. The method of Embodiment 4, wherein the spacer is positioned so that the edge extends across the opposite pair of connective necks of the second electrode such that the second and third body portions of the second electrode are located entirely within the capillary channel.

6. The method of Embodiment 4, wherein the spacer is positioned so that the edge extends across the opposite pair of connective necks of the second electrode and partially overlaps the third body portion of the second electrode.

7. The method of Embodiments 1 to 6, wherein each one of the opposite pair of connective necks extends from the second body portion to an electrode lead on the electrode-support substrate so that each one of the opposite pair of connective necks provides an electrical connection between the second electrode and at least one contact configured to connect the test element to a meter.

8. A method of verifying test element integrity of a test element having an integrity electrode, the method comprising:
providing a test element comprising (a) a cover; (b) an electrode-support substrate including a capillary channel defined thereon and formed in part with the cover, (c) a first electrode provided on the electrode-support substrate, at least a portion of the first electrode formed in the capillary channel, (d) at least two sample sufficiency electrodes provided on the electrode-support substrate, each of the sample sufficiency electrodes being positioned along a respective side edge of the electrode-support substrate, wherein the sample sufficiency electrodes define a gap therebetween, and (e) an integrity electrode on the electrode-support substrate in the capillary channel, wherein the integrity electrode is coupled to and extends between the at least two sample sufficiency electrodes wherein the integrity electrode and the at least two sample sufficiency electrodes surround the first electrode in the capillary channel forming a loop circuit around the first electrode; and
applying a signal across the at least two sample sufficiency electrodes to verify continuity across the integrity electrode.

9. The method of Embodiment 8, where the test element further comprises a spacer positioned on the electrode-support substrate, the spacer including an edge defining a boundary of the capillary channel on the electrode-support substrate.

10. The method of Embodiments 8 or 9, wherein the capillary channel is located at a first end of the electrode-support substrate, the capillary channel including an inlet at the first end between the electrode-support substrate and the cover.

11. The method of Embodiments 8 to 10 further comprising applying an overvoltage across the at least two sample sufficiency electrodes to burn out and open the integrity electrode.

12. The method of Embodiments 8 to 11, wherein the test element further comprises providing at least one second electrode on the electrode-support substrate.

13. The method of Embodiment 12, wherein the at least one second electrode is positioned between the first electrode and the integrity electrode.

14. A test element comprising:
a cover;

an electrode-support substrate comprising a capillary channel defined thereon defined thereon and formed in part with the cover at a first end of the electrode-support substrate;

a first electrode disposed on the electrode-support substrate, the first electrode comprising a first body portion and a connective neck extending from the first body portion;

a second electrode disposed on the electrode-support substrate, the second electrode comprising a second body portion and at least two connective necks, each one of the at least two connective necks extending from a respective end of the second body portion; and a spacer positioned on the electrode-support substrate, the spacer including an edge defining a boundary of the capillary channel, wherein the cover is coupled to the spacer, wherein the second body portion of the second electrode and the at least two connective necks form a U-shaped loop circuit surrounding the first electrode, the second electrode configured to provide an indication of continuity to verify test element integrity.

15. The test element of Embodiment 14, wherein the capillary channel comprises an inlet at the first end of the electrode-support substrate, the edge of the spacer extending between opposite side edges of the electrode-support substrate.

16. The test element of Embodiments 14 or 15, wherein the second electrode further comprises a third body portion positioned adjacent the first body portion of the first electrode opposite the second body portion of the second electrode, the third body portion coupled to one of the at least two connective necks.

17. The test element of Embodiment 16, wherein the edge of the cover extends across the at least two connective necks of the second electrode such that the second and third body portions of the second electrode are located entirely within the capillary channel.

18. The test element of Embodiment 16, wherein the edge of the spacer extends across the at least two connective necks of the second electrode and partially overlaps the third body portion of the second electrode.

19. The test element of any one of Embodiments 16 to 18 further comprising at least two sample sufficiency electrodes disposed on the electrode-support substrate, each one of the sample sufficiency electrodes being positioned along a respective side edge of the electrode-support substrate.

20. The test element of any one of Embodiments 16 to 19, further comprising an integrity electrode disposed on the electrode-support substrate, the integrity electrode coupled to and extending between the at least two sample sufficiency electrodes, the integrity electrode configured to provide an indication of continuity to verify test element integrity.

21. A method of verifying test element integrity as substantially described and shown herein.

22. An test element having an integrity electrode arrangement as substantially described and shown herein.

The invention claimed is:

1. A method of verifying test element integrity of a test element having an integrity electrode, the method comprising:

providing a test element comprising (a) an electrode-support substrate, (b) a working electrode provided on the electrode-support substrate that includes a first body portion and a first connective neck extending from the first body portion, (c) a counter electrode provided on the electrode-support substrate that includes a second body portion, an opposite pair of second connective necks, and a third body portion coupled to one of the opposite pair of second connective necks and positioned adjacent the first body portion of the working electrode opposite the second body portion, each of the opposite pair of second connective necks extending transversely from a respective end of the second body portion, (d) a cover, and (e) a spacer coupled to the electrode-support substrate and partially overlapping the third body portion of the counter electrode, the spacer including an edge defining a boundary of a capillary channel formed between the cover and the electrode-support substrate, wherein each of the opposite pair of second connective necks extend across the boundary of the capillary channel free from the second body portion and the third body portion such that the second body portion is located entirely within the capillary channel, and the second body portion and the opposite pair of second connective necks surround the working electrode in the capillary channel forming a loop circuit around the working electrode; and applying a signal across the pair of connective necks of the counter electrode to verify continuity along the counter electrode.

2. The method of claim 1, wherein the first connective neck of the working electrode extends across the boundary of the capillary channel such that the first body portion of the working electrode is located entirely within the capillary channel.

3. The method of claim 1, wherein the third body portion of the counter electrode is located entirely within the capillary channel.

4. The method of claim 1, wherein one of the opposite pair of second connective necks extends from the second body portion to an electrode lead on the electrode-support substrate so that each of the opposite pair of second connective necks provides an electrical connection between the counter electrode and at least one contact configured to connect the test element to a meter.

5. A method of verifying test element integrity of a test element having an integrity electrode, the method comprising:

providing a test element comprising (a) a cover; (b) an electrode-support substrate including a capillary channel defined thereon and formed in part with the cover, (c) a working electrode provided on the electrode-support substrate, at least a portion of the working electrode located in the capillary channel, (d) at least two sample sufficiency electrodes provided on the electrode-support substrate, each of the sample sufficiency electrodes being positioned along a respective side edge of the electrode-support substrate, wherein the sample sufficiency electrodes define a gap therebetween, (e) an integrity electrode on the electrode-support substrate in the capillary channel, wherein the integrity electrode is coupled to and extends between the at least two sample sufficiency electrodes wherein the integrity electrode and the at least two sample sufficiency electrodes surround the working electrode in the capillary channel forming a loop circuit around the working electrode, and (f) a counter electrode provided on the electrode-support substrate, the counter electrode including a body portion located entirely within the capillary channel and an opposite pair of connective necks extending transversely from the body portion; and applying a signal across the at least two sample sufficiency electrodes to verify continuity across the integrity electrode.

6. The method of claim 5, where the test element further comprises a spacer positioned on the electrode-support substrate, the spacer including an edge defining a boundary of the capillary channel on the electrode-support substrate.

7. The method of claim 6, wherein the capillary channel is located at a first end of the electrode-support substrate, the capillary channel including an inlet at the first end between the electrode-support substrate and the cover.

8. The method of claim 5 further comprising applying an overvoltage across the at least two sample sufficiency electrodes to burn out and open the integrity electrode.

9. The method of claim 5, wherein the test element further comprises providing another counter electrode on the electrode-support substrate, at least a portion of the other counter electrode located in the capillary channel.

10. The method of claim 5, wherein the counter electrode is positioned between the working electrode and the integrity electrode.

11. A test element comprising:
a cover;
an electrode-support substrate comprising a capillary channel defined thereon and formed in part with the cover at a first end of the electrode-support substrate;
a working electrode disposed on the electrode-support substrate, the working electrode comprising a first body portion and a first connective neck extending from the first body portion;
a counter electrode disposed on the electrode-support substrate and operatively connected to one or more electrode traces that are operatively coupled to another counter electrode, the counter electrode comprising a second body portion, at least two second connective necks, and a third body portion coupled to one of the at least two second connective necks and positioned adjacent the first body portion of the working electrode opposite the second body portion, each of the at least two second connective necks extending transversely from a respective end of the second body portion; and
a spacer positioned on the electrode-support substrate, the spacer including an edge defining a boundary of the capillary channel, wherein the cover is coupled to the spacer,
wherein the first body portion of the working electrode includes an end extending toward the boundary of the capillary channel, each of the at least two second connective necks extend across the boundary of the capillary channel free from the second body portion and the third body portion such that the second body portion is located entirely within the capillary channel, and the second body portion and the at least two second connective necks form a loop circuit surrounding the working electrode.

12. The test element of claim 11, wherein the capillary channel comprises an inlet at the first end of the electrode-support substrate, the edge of the spacer extending between opposite side edges of the electrode-support substrate.

13. The test element of claim 11, wherein the third body portion of the counter electrode is located entirely within the capillary channel.

14. The test element of claim 11, wherein the spacer partially overlaps the third body portion of the counter electrode.

15. The test element of claim 11 further comprising at least two sample sufficiency electrodes disposed on the electrode-support substrate, each of the sample sufficiency electrodes being positioned along a respective side edge of the electrode-support substrate.

16. The test element of claim 15, further comprising an integrity electrode disposed on the electrode-support substrate, the integrity electrode coupled to and extending between the at least two sample sufficiency electrodes, the integrity electrode configured to provide an indication of continuity to verify test element integrity.

* * * * *